US009429539B2

(12) United States Patent
Van Grinsven et al.

(10) Patent No.: US 9,429,539 B2
(45) Date of Patent: Aug. 30, 2016

(54) BIOSENSOR USING IMPEDIMETRIC REAL-TIME MONITORING

(71) Applicants: IMEC, Leuven (BE); Universiteit Hasselt, Hasselt (BE)

(72) Inventors: Bart Van Grinsven, Heerlen (NL); Ward De Ceuninck, Nerem (BE); Patrick Wagner, Vilvoorde (BE)

(73) Assignees: IMEC, Leuven (BE); Universiteit Hasselt, Hasselt (BE)

( * ) Notice: Subject to any disclaimer, the term of this patent is extended or adjusted under 35 U.S.C. 154(b) by 0 days.

(21) Appl. No.: 14/567,792

(22) Filed: Dec. 11, 2014

(65) Prior Publication Data

US 2015/0219584 A1 Aug. 6, 2015

Related U.S. Application Data

(62) Division of application No. 13/991,223, filed as application No. PCT/EP2011/071090 on Nov. 25, 2011, now Pat. No. 8,932,868.

(60) Provisional application No. 61/421,143, filed on Dec. 8, 2010.

(51) Int. Cl.
G01N 15/06 (2006.01)
G01N 33/00 (2006.01)
(Continued)

(52) U.S. Cl.
CPC ......... *G01N 27/327* (2013.01); *B01L 3/50273* (2013.01); *B01L 3/502738* (2013.01);
(Continued)

(58) Field of Classification Search
CPC ....... G01N 15/06; G01N 33/00; G01N 33/48
USPC .......... 422/50, 68.1, 82.01, 82.02, 502, 503; 436/43, 94, 89
See application file for complete search history.

(56) References Cited

U.S. PATENT DOCUMENTS 6,355,431 B1 * 3/2002 Chee et al. ................ 435/6.11
7,001,792 B2 * 2/2006 Sauer et al. ................. 438/49
(Continued)

FOREIGN PATENT DOCUMENTS

| WO | 2004/079001 A1 | 9/2004 |
| WO | 2006/027582 A1 | 3/2006 |
| WO | 2007/068719 A1 | 6/2007 |

OTHER PUBLICATIONS

PCT International Search Report, PCT International Application No. PCT/EP2011/071090, dated Apr. 2, 2012.
(Continued)

*Primary Examiner* — Brian J Sines
(74) *Attorney, Agent, or Firm* — McDonnell Boehnen Hulbert & Berghoff LLP

(57) ABSTRACT

A method an system is disclosed for the detection and/or allocation of at least one point mutation in target DNA and/or RNA duplexes. The method comprises obtaining a functionalized surface which is coated with probe DNA and/or RNA whereto target DNA and/or RNA duplexes are attached, contacting said functionalized surface to an electrolytic solution having a neutral pH in a flow cell and measuring a first impedance value within said electrolytic solution, and then adding a chemical to the electrolytic solution which is able to achieve denaturation of the target DNA and/or RNA. The method further comprises measuring a second impedance value within the flow cell after completion of the denaturation of the DNA and/or RNA target, and then obtaining a value representative for the impact of the chemical on the impedance of the electrolytic solution. The amount and/or allocation of point mutation(s) within the target DNA and/or RNA is then determined by calculating the denaturation-time constant based on the difference between the first and second impedance value and taking into account the impact of the chemical by third impedance value.

15 Claims, 5 Drawing Sheets

(51) Int. Cl.
| | |
|---|---|
| G01N 33/48 | (2006.01) |
| G01N 27/327 | (2006.01) |
| C12Q 1/68 | (2006.01) |
| G01N 27/02 | (2006.01) |
| B01L 3/00 | (2006.01) |
| G05B 15/02 | (2006.01) |

(52) U.S. Cl.
CPC ........... *C12Q1/6825* (2013.01); *C12Q 1/6827* (2013.01); *C12Q 1/6832* (2013.01); *G01N 27/021* (2013.01); *G01N 27/3275* (2013.01); *G05B 15/02* (2013.01); *B01L 2300/023* (2013.01); *B01L 2300/0636* (2013.01); *Y10T 436/11* (2015.01); *Y10T 436/143333* (2015.01)

(56) References Cited

U.S. PATENT DOCUMENTS

| | | | |
|---|---|---|---|
| 7,122,152 B2* | 10/2006 | Lewis et al. | 422/50 |
| 7,157,232 B2* | 1/2007 | Miles et al. | 506/39 |
| 8,021,845 B2* | 9/2011 | Hirai et al. | 435/6.12 |
| 8,703,928 B2 | 4/2014 | Barany et al. | |
| 8,802,373 B2 | 8/2014 | Barany et al. | |
| 8,932,868 B2* | 1/2015 | Van Grinsven et al. | 436/94 |
| 8,945,912 B2* | 2/2015 | Bashir et al. | 435/287.2 |
| 2005/0026202 A1 | 2/2005 | Edman et al. | |
| 2007/0054299 A1 | 3/2007 | Heller et al. | |
| 2012/0021918 A1* | 1/2012 | Bashir et al. | 506/2 |
| 2014/0011198 A1 | 1/2014 | Van Grinsven et al. | |

OTHER PUBLICATIONS

Pote, John et al., "Kinetics of Mass and DNA Decomposition in Tomato Leaves", Chemosphere, vol. 61, May 5, 2005, pp. 677-684.
Wang, Xiaoyu et al., "UV-Induced Grafting of Alkenes to Silicon Surfaces: Photoemission Versus Exciton", J. Am. Chem. Soc., vol. 132, 2010, pp. 4048-4049.
Clarke, James et al., "Continuous Base Identification for Single-Molecule Nanopore DNA Sequencing", Nature Nanotechnology, vol. 4, Apr. 2009, pp. 265-270.
Van Grinsven, B. et al., "Rapid Assessment of the Stability of DNA Duplexes by Impedimetric Real-Time Monitoring of Chemically Induced Denaturation", Lab on a Chip, vol. 11, No. 9, Jan. 1, 2011, pp. 1656-1663.
Park, Jin-Young et al., "DNA Hybridization Sensors Based on Electrochemical Impedance Spectroscopy as a Detection Tool", Sensors, vol. 9, No. 12, Jan. 1, 2009, pp. 9513-9532.
Davis, Frank et al., "Single Gene Differentiation by DNA-Modified Carbon Electrodes Using an AC Impedimetric Approach", Analytical Chemistry, vol. 79, No. 3, Feb. 1, 2007, pp. 1153-1157.
Hooyberghs, J. et al., "Breakdown of Thermodynamic Equilibrium for DNA Hybridization in Microarrays", Physical Review, vol. 81, Jan. 13, 2010, pp. 012901-1-012901-4.
Tindall, Elizabeth A. et al., "Assessing High-Resolution Melt curve Analysis for Accurate Detection of Gene Variants in Complex DNA Fragments", Human Mutation, vol. 30, Mar. 11, 2009, pp. 876-883.
Lodewyckx, L. et al., "Mutation Detection in the Alpha-1 Antitrypsin Gene (PI) Using Denaturing Gradient Gel Electrophoresis", Human Mutation, vol. 18, Apr. 27, 2001, pp. 243-250.
Rant, Ulrich et al., "Switchable DNA Interfaces for the Highly Sensitive Detection of Label-Free DNA Targets", Proceedings of the National Academy of Sciences of the United States of America, vol. 104, No. 44, Oct. 30, 2007, pp. 17364-17369.
Ingebrandt, S. et al., "Label-Free Detection of Single Nucleotide Polymorphisms Utilizing the Differential Transfer Function of field-Effect Transistors", Biosensors and Bioelectronics, vol. 22, 2007, pp. 2834-2840.
Poghossian, A. et al., "Possibilities and Limitations of Label-Free Detection of DNA Hybridization With Field-Effect-Based Devices", Sensors and Actuators, Apr. 30, 2005, pp. 470-480.
Vermeeren, V. et al., "Towards a Real-Time, Label-Free, Diamond-Based DNA Sensor", Langmuir, vol. 23, Sep. 20, 2007, pp. 13193-13202.
Yang, Nianjun et al., "Vertically Aligned Diamond Nanowires for DNA Sensing", Angewandte Chemie, vol. 47, 2008, pp. 5183-5185.
Wenmackers, Sylvia et al., "Diamond-Based DNA Sensors: Surface Functionalization and Read-Out Strategies", Phys. Status Solidi, vol. 206, No. 3, Jan. 26, 2009, pp. 391-408.
Gu, Huiru et al., "Electrochemical Impedance Sensing of DNA Hybridization on Conducting Polymer Film-Modified Diamond", Journal of Physical Chemistry, vol. 109, Apr. 11, 2005, pp. 13611-13618.
Williams, O.A. et al., "Growth, Electronic Properties and Applications of Nanodiamond", Diamond & Related Materials, vol. 17, Feb. 13, 2008, pp. 1080-1088.
Vermeeren, V. et al., "Topographical and Functional Characterization of the ssDNA Probe Layer Generated Through EDC-Mediated Covalent Attachment to Nanocrystalline Diamond Using Fluorescence Microscopy", Langmuir, vol. 24, May 22, 2008, pp. 9125-9134.
Leber, Markus et al., "A Fractional Programming Approach to Efficient DNA Melting Temperature Calculation", Bioinformatics, vol. 21, No. 10, Mar. 15, 2005, pp. 2375-2382.
John SantaLucia Lab, http://ozone3.chem.wayne.edu, printed Jun. 4, 2014.

* cited by examiner

BIOSENSOR USING IMPEDIMETRIC REAL-TIME MONITORING

CROSS-REFERENCE TO RELATED APPLICATIONS

This application is a divisional of U.S. patent application Ser. No. 13/991,223, filed Jun. 3, 2013, which is a U.S. National Phase Application of International Patent Application No. PCT/EP2011/071090 filed on Nov. 25, 2011, which claims the benefit of priority of U.S. Provisional Patent Application Ser. No. 61/421,143, filed Dec. 8, 2010, each of which is hereby incorporated by reference in its entirety.

FIELD OF THE INVENTION

The present disclosure is related to detection and/or characterisation of particles such as biomolecules such as DNA or RNA bioparticles. More particular, the present invention relates to a method and system for detecting or characterizing particles such as biomolecules, e.g. for detecting of point mutations in DNA and/or RNA bioparticles. Furthermore, the present disclosure relates to a biosensor device using impedimetric real time monitoring. More particular, the present invention relates to a bio-sensing device thereby using chemically induced denaturation of DNA and/or RNA bioparticles and monitoring said denaturation by impedance spectroscopy.

BACKGROUND OF THE INVENTION

Single-nucleotide polymorphisms (SNPs) in DNA duplexes in human genomics play a key role in several hundreds of diseases. One of the central challenges is the detection and identification of these SNPs and miniaturized assays such as microarrays play an important role to allow for a massively parallelized readout in combination with limited sample volumes [Ng et al., Analytical and Bioanalytical Chemistry 386, p 427 (2006)]. Disadvantages are the long reaction times at the scale of at least 16 hours, the complete lack of dynamic information on the DNA binding kinetics, the need for fluorescent labelling of the target DNA, and the sophisticated optical readout techniques. Also, microarrays are in principle limited to the detection of known mutations albeit there is recent progress to exploit the thermodynamic aspects of probe DNA-target DNA recognition to identify SNPs even in the presence of wild-type DNA [Hooyberghs et al., Physical Review E 81, 012901 (2010)].

Alternatively, mutation analysis can be performed using techniques that exploit the denaturation of double-stranded (ds) DNA rather than the hybridization process. The best known examples are real-time PCR (polymerase chain reaction) with associated melting-curve analysis [Tindall et al., Human Mutation 30, p 876 (2009)] and denaturing gradient gel electrophoresis DGGE [Lodewyckx et al., Human Mutation 18, p 243 (2001)]. Both techniques rely on the fact that DNA duplexes containing a SNP are less stable than complementary duplexes. This leads to lower denaturation (melting) temperatures for SNP-type DNA duplexes as compared to the complementary duplexes. Nevertheless, both techniques require expensive instrumentation, real-time PCR relies on the use of fluorescent labels, and DGGE is not suitable for high-throughput analysis.

Due to the inherent complexity of microarrays and the established denaturation-based approaches, strong efforts are put into the development of label-free detection techniques based on electronic readout principles. One of these electronic routes is the direct sequencing of DNA fragments with solid-state- and haemolysin nanopores, utilizing the current-blocking effect [Clarke et al., Nature Nanotechnology 4, 265-270 (2010)]. Alternatively, the DNA switching method on gold electrodes proposed by Rant [Rant et al., Proceedings of the National Academy of Sciences of the United States of America 104, p 17364 (2007] allows for real-time monitoring of hybridization and denaturation with the possibility to distinguish between complementary and mismatched fragments. Despite the method requires no fluorescent labelling of the target DNA, labels are involved on the probe DNA.

A method without any labelling and auxiliary chemistry is the solution-gate field-effect transistor (FET) device with the probe DNA directly immobilized on the gate oxide [Ingebrandt et al Biosensors and Bioelectronics 22, p 2834 (2007)]. Real-time monitoring of hybridization is in principle possible and the FETs can discriminate between complementary and mismatched strands under ex situ conditions. The sensing effect of FETs is attributed to the intrinsic negative charge of ss- and ds-DNA fragments and to a redistribution of ionic charges at the proximity of the gate insulator during hybridization [Poghossian et al., Sensors and Actuators B—Chemical 111, p 470 (2005)].

DNA-hybridization sensors based on impedance spectroscopy have been established with screen-printed carbon electrodes [Davis et al., Analytical Chemistry 79, 1153-1157 (2007)], mixed self-assembled monolayers on gold electrodes using a redox system, conjugated polymers, and GaN nanowires [Park et al., Sensors 9, 9513-9532 (2009)].

Despite of all recent progress, the aforementioned electronic- or opto-electronic methods for DNA sensing have in common that there are at least two or more of the following drawbacks:
    need for high-end instrumentation and incompatibility with upgrading towards high-throughput assays;
    need for additional chemicals such as fluorescent dyes or redox mediators;
    lack of sensor-regeneration capacity;
    missing proof that the sensor response is intrinsic and unaffected by conductivity effects related to temperature or ionic composition of the buffer liquids;
    insufficient statistics to demonstrate the reproducibility;
    lack of dynamic information on the kinetics of hybridization- or denaturation events.

As a conclusion, the state of the art techniques used in genetic research laboratories do not meet the criteria of being label-free, fast and cheap. Furthermore, these techniques allow only for single-term measurements and cannot be used repetitively. There is hence still a need to further elaborate the detection and identification of single-nucleotide polymorphisms (SNPs).

SUMMARY OF THE INVENTION

It is an object of embodiments of the present invention to provide a method and a sensing device for the detection and/or characterization of biomolecules which is label-free and reliable. It is an advantage of embodiments of the present invention that a reliable detection and/or characterisation can be obtained in a fast way. It furthermore is an advantage of embodiments of the present invention that the detection and/or characterization can be obtained in a cheap way.

It is an advantage of embodiments of the present invention that a method and sensing device for the detection and/or allocation of point mutations in DNA and/or RNA bioparticles can be provided, whereby the sensor used for the detection and characterization is suitable for multiple-term measurements and can be used repetitively, i.e. is re-usable.

It is an advantage of embodiments of the present invention that a sensing device can be obtained that works as a cartridge and a reader, so that only the cartridge needs to be replace, resulting in an economically interesting device.

The above object is accomplished by a method and device according to the present invention.

The present invention relates to a method for the detection and/or allocation of at least one point mutation in target DNA and/or RNA duplexes, said method comprising at least the steps of obtaining a functionalized surface which is coated with probe DNA and/or RNA whereto the target DNA and/or RNA duplexes are attached, contacting said functionalized surface to an electrolytic solution having a neutral pH in a flow cell and measuring a first impedance value within said electrolytic solution, and then adding a chemical to the electrolytic solution which is able to achieve denaturation of the target DNA and/or RNA. The method further comprises then measuring a second impedance value within the flow cell after completion of the denaturation of the DNA and/or RNA target, then obtaining a value representative for the impact of the chemical on the impedance of the electrolytic solution, and then determining the amount and/or allocation of point mutation(s) within the target DNA and/or RNA by calculating the denaturation-time constant based on the difference between the first and second impedance value and corrected for the impact of the chemical by the value representative therefore.

Obtaining a functionalized surface, or a substrate comprising such a surface, which is coated with probe DNA and/or RNA whereto the target DNA and/or RNA duplexes are attached may comprise providing a functionalized surface which is coated with probe DNA and/or RNA and attaching target DNA and/or RNA duplexes to the probes. Obtaining a functionalised surface, or a substrate comprising such a surface, thus also may comprise may comprise attaching the target DNA and/or RNA duplexes to a functionalized surface which is coated with probe DNA and/or RNA. Obtaining a functionalized surface, or a substrate comprising such a surface, alternatively may be receiving such a surface after the target DNA and/or RNA duplexes have been attached.

Obtaining a value representative for the impact of the chemical on the impedance of the electrolytic solution may comprise, after measuring a second impedance value, removing the chemical from the flow cell by adding electrolytic solution and then measuring a third impedance value within the flow cell to determine the impact of the chemical on the impedance of the electrolytic solution, the third impedance value being the value representative for the impact of the chemical on the impedance of the electrolytic solution.

The functionalized surface may be provided on a substrate which is biocompatible and chemically and physically stable at elevated temperatures in extreme pH conditions and in solutions with high ionic strengths.

The substrate may be nanocrystalline diamond (NCD).

The substrate may be a semiconductor substrate having a diamond coating with a thickness between 50 nm and 150 nm, e.g. about 100 nm, e.g. 100 nm, on at least one of its surface.

The functionalized surface may comprise a first layer of fatty acid(s) such as 10-undecenoic fatty acid.

The functionalized surface may comprise a second layer provided onto said first layer and containing the probe DNA and/or RNA.

The probe DNA may be NH2-modified single stranded DNA (ssDNA). Attaching the target DNA duplexes to the functionalized surface may be performed by hybridization of the target DNA with the probe ssDNA molecules.

The chemical may be NaOH, preferably in a concentration of around 0.1 M.

The present invention also relates to a bio-sensing device suitable for the detection of DNA and/or RNA and/or the characterization (allocation) of point mutations in DNA and/or RNA, said bio-sensing device comprising at least a flow cell equipped with an impedimetric analyzer, a slit for inserting a biocompatible and inert substrate so that it is exposed by at least one surface of said substrate to the flow cell and having covalently bounded probe DNA and/or RNA on its exposed surface and suitable for attaching target DNA and/or RNA to said probe DNA and/or RNA, or alternatively a biocompatible and inert substrate so that it is exposed by at least one surface of said substrate to the flow cell and having covalently bounded probe DNA and/or RNA on its exposed surface and suitable for attaching target DNA and/or RNA to said probe DNA and/or RNA, a pumping system and switching valve connected to said flow cell a first liquid supply comprising a electrolytic solution connected to said pumping system and switching valve a second liquid supply comprising a chemical which is able to achieve denaturation of DNA and/or RNA such that the target DNA and/or RNA is released from the probe DNA and/or RNA connected to said pumping system and switching valve. The biosensing device advantageously also may comprise a means for obtaining a value representative for the impact of the chemical on the impedance of the electrolytic solution.

The means for obtaining a value representative for the impact of the chemical on the impedance of the electrolytic solution may be a controller programmed for controlling the impedance analyzer and the pumping system and switching valve for removing the chemical from the flow cell by adding electrolytic solution and then measuring a third impedance value within the flow cell to determine the impact of the chemical on the impedance of the electrolytic solution, the third impedance value being the value representative for the impact of the chemical on the impedance of the electrolytic solution.

The present invention also relates to a controller for controlling a bio-sensing device suitable for the detection of DNA and/or the characterization (allocation) of point mutations in DNA, the controller being programmed for providing control signals to the bio-sensing device for contacting a functionalized surface which is coated with probe DNA and/or RNA whereto target DNA and/or RNA duplexes are attached with an electrolytic solution having a neutral pH in a flow cell and measuring a first impedance value within said electrolytic solution, then adding a chemical to the electrolytic solution which is able to achieve denaturation of the target DNA and/or RNA, then measuring a second impedance value within the flow cell after completion of the denaturation of the DNA target, then obtaining a value representative for the impact of the chemical on the impedance of the electrolytic solution, and then determining the amount and/or allocation of point mutation(s) within the target DNA and/or RNA by calculating the denaturation-time constant based on the difference between the first and second impedance value and corrected for the impact of the chemical by the value representative therefore.

The controller may be a computer program product. Such a computer program product may result in, when run on a processor, the bio-sensing device performing the actions as indicated above.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

All figures are intended to illustrate some aspects and preferred embodiments. The figures are depicted in a simplified way for reason of clarity. Not all alternatives and options are shown and the invention is not limited to the content of the given drawings. Like numerals are employed to reference like parts in the different figures.

DEFINITIONS

Figure 1:
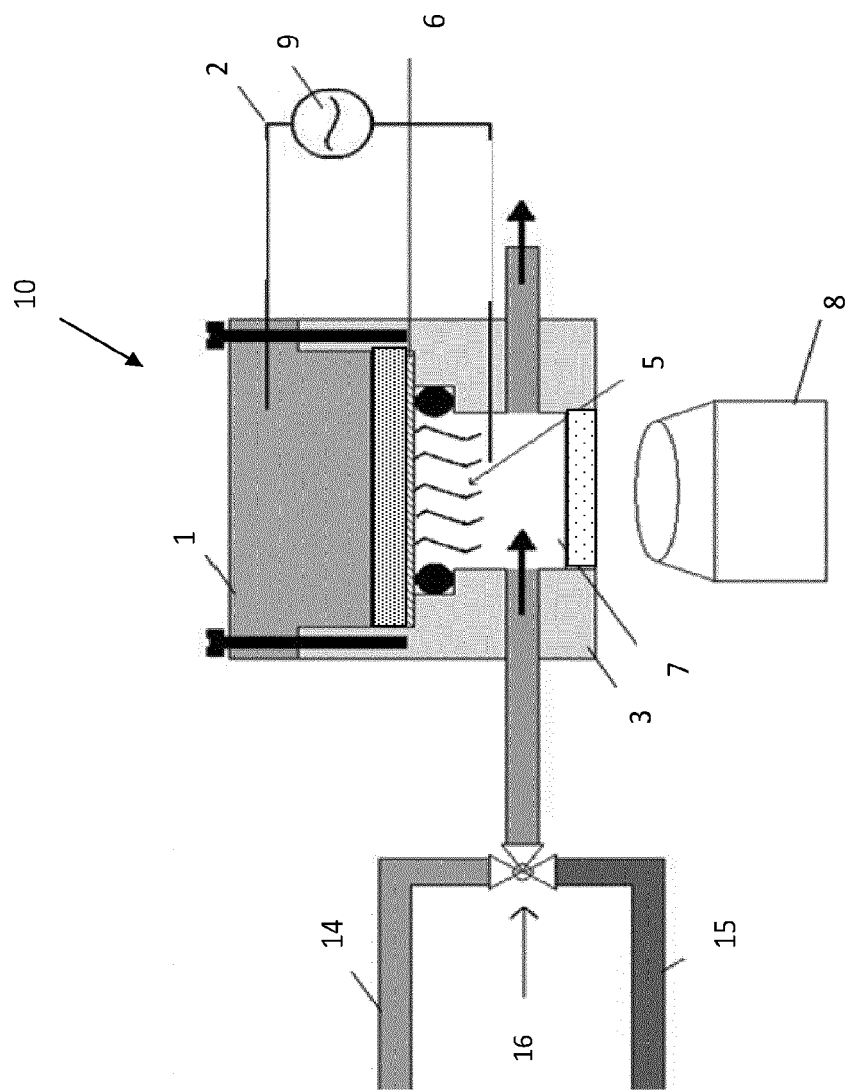
FIG. 1 illustrates a schematic view of the impedimetric flow cell according to an exemplary embodiment of the invention with the DNA-carrying diamond electrode, counter electrode, optical access and pumping system for PBS buffer and NaOH as denaturation agent.

The term "DNA denaturation" as referred to in the claims and the description is used to define the process by which double-stranded DNA unwinds and separates into single-stranded DNA through the breaking of hydrogen bonding between the bases. Throughout the description said denaturation process refers to the separation of DNA strands induced by chemicals, preferably by NaOH.

The term "DNA Hybridization" as referred to in the claims and the description is used to define the process of establishing a non-covalent, sequence-specific interaction between two or more complementary strands of nucleic acids into a single hybrid, which in the case of two strands is referred to as a duplex. Oligo-nucleotides, DNA, or RNA will bind to their complement under normal conditions, so two perfectly complementary strands will bind to each other readily.

The term "single-nucleotide polymorphism" refers to a DNA sequence variation occurring when a single nucleotide—A, T, C, or G—in the genome differs between members of a species or paired chromosomes in an individual.

The term "denaturation time constant" refers to the time needed Time needed to unfold the double helix structure of the DNA sequences, in the sense that the covalently attached probe-DNA sequence stays on the diamond surface.

The term "deconvolution" as referred to in this application is to be interpreted as a mathematical operation on an original function as will be disclosed in Fit equation [1], thereby producing a third Fit equation [3] as will be disclosed that is a modified version of the original equation and which will reveal the final denaturation time.

Embodiments of the present invention and examples thereof will mainly be described with reference to detection of DNA and/or characterisation of point mutations of DNA, but are equally applicable—mutates mutandis—to detection of RNA and/or characterisation of RNA

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Moreover, the term top and the like in the description and the claims are used for descriptive purposes and not necessarily for describing relative positions. It is to be understood that the terms so used are interchangeable under appropriate circumstances and that the preferred embodiments described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary preferred embodiments, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that preferred embodiments may be practiced without these specific details. In other instances, well-known methods, structures and techniques have not been shown in detail in order not to obscure an understanding of this description.

The invention will now be described by a detailed description of several preferred embodiments. It is clear that other preferred embodiments can be configured according to the knowledge of persons skilled in the art without departing from the true spirit or technical teaching of the invention as defined by the appended claims.

It is an object of preferred embodiments to further elaborate the detection and identification of single-nucleotide polymorphisms (SNPs) in DNA duplexes. State of the art techniques do not satisfy the criteria of being of being label-free, fast (high throughput) and cheap. Furthermore none of the state of the art techniques is suitable for performing multiple analyses.

The problem of state of the art techniques is solved by measuring the impedance before and after chemically-induced DNA and/or RNA denaturation of target DNA and/or RNA in a impedimetric flow cell. The monitoring of chemically induced denaturation in an impedimetric flow cell by investigating the variation in impedance in said flow cell make it possible to detect not only the presence of point mutation (single-nucleotide polymorphisms) but also the location of said point mutation in the target DNA and/or RNA. Moreover, this can be performed in an accurate manner according to embodiments of the present invention. According to a first aspect of the invention, a method for the detection and/or characterization of bioparticles, e.g. biomolecules thereby using impedance measurements is disclosed.

According to embodiments the method for the detection and/or characterization of bioparticles comprises the detection and/or allocation of point mutation in target DNA and/or RNA duplexes. The method for the detection and/or allocation of at least one point mutation in target DNA and/or RNA duplexes comprises the step of obtaining a functionalized surface which is coated with probe DNA and/or RNA whereto the target DNA and/or RNA duplexes are attached. The latter may be by performing the actions of providing a functionalized surface coated with probe DNA and/or RNA and attaching target DNA and/or RNA duplexes thereto. Alternatively, the latter may be obtained by receiving the functionalized surface with coated probe DNA and/or RNA and target DNA and/or RNA duplexes already attached thereto. Such receiving may be positioning the functionalized surface, or more generally the substrate comprising the functionalized surface, in the biosensor device. The biosensor may be a cartridge system and the substrate may be a disposable substrate, insertable in the biosensor. The biosensor therefore may comprise a disposable substrate holder or a slit for inserting the disposable substrate. Alternatively, the substrate may be a cleanable substrate, allowing to clean and re-use the substrate or at least the portion of the substrate comprising e.g. more expensive components such as for example a nanocrystalline diamond layer. The method also comprises contacting the functionalized surface to an electrolytic solution having a neutral pH in a flow cell and measuring a first impedance value within said electrolytic solution. The method thereafter comprises adding a chemical to the electrolytic solution which is able to achieve denaturation of the target DNA and/or RNA and then measuring a second impedance value within the flow cell after completion of the denaturation of the DNA and/or RNA target. Another step of the method comprises obtaining a value representative for the impact of the chemical on the impedance of the electrolytic solution. This can be receiving such a value based on a previously performed experiment, a reference measurement or a theoretical or experimental value, e.g. retrieved from a memory or look-up-table. Alternatively, the value may be determined through measurement, i.e. by performing, after determination of the second impedance value, the steps of removing the chemical from the flow cell by adding electrolytic solution and measuring a third impedance value within the flow cell thereafter to determine the impact of the chemical on the impedance of the electrolytic solution. The third impedance value then may be or may be a basis for the value representative for the impact of the chemical on the impedance of the electrolytic solution. In still a further step, the method according to embodiments of the present invention comprises determining the amount and/or allocation of point mutation(s) within the target DNA and/or RNA by calculating the denaturation-time constant based on the difference between the first and second impedance value and corrected for the impact of the chemical by the value representative therefore.

According to some embodiments, the functionalized surface is provided on a suitable substrate. The substrate may be intrinsically biocompatible and being chemically and physically stable at elevated temperatures, under extreme pH conditions, and in solutions with high ionic strengths.

According to some embodiments, the substrate with a functionalized surface is nanocrystalline diamond (NCD). NCD is a universal electrode material known in the art for monitoring biochemical reactions in real time. DNA-hybridization sensors based on diamond as a platform material have been reported in combination with impedance spectroscopy [Vermeeren et al., Langmuir 23, p 13193 (2007)]. Alternative materials providing similar conditions as the nanocrystalline diamond may for example also be used. Some other examples of materials that could be used are gold, platinum, palladium, silica and/or silicium.

According to some embodiments, the substrate with a functionalized surface has to be such that it allows for the covalent immobilization of biochemical receptors.

According to some embodiments, the substrate with a functionalized surface may be a silicon wafers which may be diced into samples of suitable dimensions to fit in the impedimetric flow cell (e.g. 10 mm by 10 mm) having a diamond coating on at least one of its surface. Said diamond coating (layer) may have a typical thickness between e.g. 50 nm and 300 nm, e.g. between 100 nm and 300 nm, e.g. around 100 nm.

By way of illustration, embodiments of the present invention not being limited thereto, the functionalized surface comprises a first layer of fatty acid(s), e.g. 10-undecenoic fatty acid which may be photochemically attached to the at least one surface of the substrate e.g. to a H-terminated NCD substrate (electrode) by UV illumination (wavelength 254 nm, intensity 265 mW/cm$^2$) during 20 hours under a protective N$_2$ atmosphere. The reaction mechanism is presumably based on the fact that the hydrophobic C=C end of the fatty acid is oriented towards the H-terminated diamond surface and mediated by photoemission from the surface as proposed for the photochemical grafting of alkenes to silicon surfaces by Wang et al. [Wang et al., Journal of the American Chemical Society 132, p 4048 (2010)]. After this photochemical treatment, the substrate may be rinsed (e.g. in an acidic acid at 100° C.) to remove unbound fatty-acid fragments. A second layer may then be provided comprising the probe DNA. Said probe DNA may be NH2-modified single stranded DNA (ssDNA) (36-mer with the sequence 5'-NH$_2$—C$_6$H$_{12}$ AAA AAA ACC CCT GCA GCC CAT GTA TAC CCC CGA ACC-3' (SEQ ID NO: 1)) which can be covalently linked to the COOH group of the fatty acid using carbodiimide coupling. The details of this procedure and the final washing steps to remove non-reacted probe DNA have been published [Vermeeren et al., Langmuir 24, p 9125 (2008)].

According to some embodiments, target DNA may be attached (provided) to the functionalized surface by means of hybridization of the target DNA with the probe ssDNA molecules being present on the functionalized surface. By way of illustration, one technique for attaching target DNA in one example may be attaching by incubating functionalized (more specific ssDNA-modified) NCD substrates for 2 hours at 30° C. with target ssDNA.

According to some embodiments, the step of calculating the denaturation-time constant comprises that at $t_0$=0 min, a chemical enters the flow cell and replaces the electrolyte (e.g. PBS) filling. The chemical may be NaOH which may have a concentration of around 0.1 M NaOH and enters the flow cell at a flow rate of around 250 μl per minute. Alternatively, also NaOH with different molarities may be used. Alternative chemicals, having a similar effect as NaOH may also be used. Some examples of alternative chemicals are dimethylsulfoxide or formamide. The chemical advantageously has an elevated pH for distorting the hydrogen bonds resulting in the denaturation. This addition of the chemical results in a variation in impedance (impedance drop). Said impedance variation (drop) contains two major separate contributions. The first contribution is due to the intrinsic effect of denaturation which affects the electronic properties in the vicinity of the topmost surface (e,g. Diamond) layer. The second contribution is due to the medium exchange as the chemical (e.g. 0.1 M NaOH) may cause a higher conductivity. To distinguish both contributions quantitatively, the chemical may be replaced by reintroducing electrolyte (e.g. 1' PBS). This is done after a time period which is sufficient to achieve denaturation of the target DNA, said time period is such that all denatured DNA is flushed out (in case the electrolyte is pumped in the flow cell at a flow rate of 0.25 ml/min this time period may be a time t1 of around 10-15 minutes). The removal of the chemical gives an increase in impedance and after a time period t2, the impedance value stabilizes at a plateau having a lower value as compared to the starting condition. This demonstrates that the impedimetric properties of the functionalized surface (electrode) have changed upon denaturation because the ionic properties of the electrolyte (e.g. PBS) are identical before and after the denaturation step. The time period needed for removal of the chemical of introducing 0.1 M NaOH may be around 10-15 min giving a stabilized impedance value e.g. at a time t2=30 min.

Without wishing to be bound by theory, the superimposed processes of denaturation and medium exchange may be mathematically be described as follows:

$$Z(t) = Z(t = \infty) + A_1 \cdot \exp\left\{-\frac{t}{\tau_1}\right\} + A_2 \cdot \exp\left\{-\frac{t}{\tau_2}\right\} \quad [1]$$

$$Z(t) = Z(t = \infty) + A_2 \cdot \exp\left\{-\frac{t - t_2}{\tau_2}\right\} \quad [2]$$

Equation [1] represents the double-exponential Fit function for the superimposed, independent decay processes. The parameter A1 represents the denaturation-related decay amplitude and $\tau_1$ the associated time constant; the amplitude A2 refers to the impedance drop by the medium exchange and x1 is the corresponding time constant. Equation [2] represents solely the influence of the medium exchange from electrolyte (e.g. 1' PBS) due to the addition of the chemical (e.g. addition of 0.1 M NaOH) after the denaturation has taken place and is therefore representative for the medium exchange as such (contribution of the chemical).

The method according to embodiments of the invention has the advantage of being label-free meaning that the target DNA and/or RNA to be measured does not have to be labelled beforehand.

The method according to embodiments of the invention has the advantage of being fast, reliable, and cheap. This is mainly due to the fact that the technique allows repetitive use of the diamond coated electrodes. The developed impedance spectroscopy unit can perform frequency sweeps from 100 Hz to 100 kHz with 10 frequencies per decade in 5.7 seconds. The entire system may be automated, this way all experiments can be performed under identical conditions, which excludes the human error.

In a second aspect, embodiments provide a sensing device suitable for detecting and/or characterizing bio-molecules.

According to particular embodiments a bio-sensing device is disclosed for the detection of DNA and/or RNA and/or the characterization (allocation) of point mutations in DNA and/or RNA. The bio-sensing device may be especially suitable for performing a method as described in the first aspect. The bio-sensing device may comprise components adapted for performing the steps of the method as described in the first aspect. According to embodiments of the present invention, the bio-sensing device comprises a flow cell equipped with an impedimetric analyzer. It further comprises a sample holder, e.g. a slit, for receiving a biocompatible and inert substrate exposed by at least one surface of said substrate to the flow cell and having covalently bounded probe DNA and/or RNA on its exposed surface and target DNA and/or RNA attached to said probe DNA and/or RNA. Alternatively the biocompatible substrate itself may be part of the bio-sensing device, optionally without the target DNA attached thereto. The bio-sensing device also comprises a pumping system and switching valve connected to the flow cell and a first liquid supply comprising an electrolytic solution connected to said pumping system and switching valve and a second liquid supply comprising a chemical which is able to achieve denaturation of DNA and/or RNA such that the target DNA and/or RNA is released from the probe DNA and/or RNA connected to said pumping system and switching valve. According to embodiments of the present invention, the bio-sensing device also comprises a means for obtaining a value representative for the impact of the chemical on the impedance of the electrolytic solution. In a particular embodiment, the means for obtaining a value representative for the impact of the chemical on the impedance of the electrolytic solution may be a controller programmed for controlling the impedance analyzer and the pumping system and switching valve for removing the chemical from the flow cell by adding electrolytic solution and then measuring a third impedance value within the flow cell to determine the impact of the chemical on the impedance of the electrolytic solution, the third impedance value being the value representative for the impact of the chemical on the impedance of the electrolytic solution. According to embodiments of the present invention, the biosensor also comprises a means for determining the amount and/or allocation of point mutation(s) within the target DNA and/or RNA by calculating the denaturation-time constant based on the difference between the first and second impedance value and corrected for the impact of the chemical by the value representative for such impact.

In some embodiments according to the present invention, the bio-sensing device may comprise or be connectable to a controller for controlling operation of the bio-sensing device. The controller may for example be adapted for providing control signals to the bio-sensing device for contacting a functionalized surface which is coated with probe DNA and/or RNA whereto target DNA and/or RNA duplexes are attached with an electrolytic solution having a neutral pH in a flow cell by controlling the valve and/or pumping system. The controller may provide control signals for measuring a first impedance value within said electrolytic solution, by controlling the impedance analyzer. The controller also may provide control signals to the valve and/or pumping system for adding a chemical to the electrolytic solution which is able to achieve denaturation of the target DNA and/or RNA. The controller further may provide control signals to the impedance analyzer for measuring a second impedance value within the flow cell after completion of the denaturation of the DNA and/or RNA target. The controller may also provide control signals for determining the amount and/or allocation of point mutation(s) within the target DNA and/or RNA by calculating the denaturation-time constant based on the difference between the first and second impedance value and corrected for the impact of the chemical by the value representative therefore. Such a value may be obtained by controlling a memory and/or processor or by controlling the valve and/or pumping system and the impedance analyzer, in case of instantaneous measurement. The impedimetric analyzer 10 comprises two electrodes and is adapted for measuring an impedance. The impedimetric analyser 10 may therefore comprise a set of electrodes, a voltage source and a current measurement unit. FIG. 1 illustrates a schematic layout of a flow cell equipped with an impedimetric analyzer 10 according to some embodiments of the invention. The working electrode (DNA 5 on nanocrystalline diamond on highly-doped silicon 6) may be additionally monitored with a fluorescence microscope 8 (e.g. for comparative reasons, i.e. such a microscope is not required for operation of embodiments of the present invention)) while a gold wire 2 serves as counter electrode. Electrodes are not limited to the types as described above. Other types of electrodes also may be used. The impedance analyser used may for example operate by applying an AC voltage at different frequencies, measuring the current and phase shift and deriving therefrom an impedance. In the current example, the impedance analyser used comprises an optional multiplexer allowing measurements in a number of channels. In the current example, the impedance analyser is based on an AD5933 chip from national instruments. The liquids (for example PBS buffer 14 and 0.1 M NaOH 15) may be sequentially administered by a syringe-driven pump system connected to a 3-way valve 16. Other types of pump systems also may be used. The temperature of the liquid in the cell 7 and of the copper back contact 1 may be measured by thermocouples (not shown). All connections to the impedance analyzer 9 are done by mini-coax cables.

The flow cell may have a variety of shapes and volumes. Volumes between 25 µl and 190 µl were tested and resulted in good measurements. If the volume is not determined by the application, the volume can be optimised—e.g. by trial and error—to obtain a good signal to noise ratio. According to some particular embodiments, the flow cell may comprise a syringe system coupled to a Perspex flow cell with a suitable inner volume. The dimensions of said inner volume are optimised towards the final device goals. To set up a test device an example was shown having a suitable inner volume of around 110 µl. The effective area of the functionalized substrate surface depends on the dimensions of the flow cell and may be in the order of around 28 mm2 exposed to the liquid. In some embodiments, the electrode may be sealed with an O-ring. A counter electrode may be added to the device, a gold wire (in one example being diameter 500 µm, oriented perpendicular with the flow direction) may be suitable for this and these may be placed at a distance of 1.7 mm from the surface of the working electrode. The working electrode may be pressed on a copper lid, serving as back electrode and heat sink together. Miniaturized thermocouples may be integrated in the copper lid and in the liquid. The cell may be, for comparative reasons as described in the examples section further on, equipped with a quartz-glass bottom, enabling simultaneous fluorescence imaging with an inverted confocal fluorescence microscope. The syringe system may comprise two identical programmable syringe pumps (ProSense, model NE-500, The Netherlands) enabling flow rates of e.g. 0.73 µl/hour to 1699 ml/hour. One syringe may serve for administering NaOH solution (e.g. 0.1 M), the other may serve for delivering the electrolyte (e.g. PBS buffer). Both syringe systems may be connected to a computer-controlled three-way valve. The impedance spectroscopy unit measures the impedance, preferably in a frequency range of 100 Hz to 100 kHz built up logarithmically with 10 frequencies per decade and a scanning speed of 5.7 s per sweep.

The system may comprise a processor. Such a processor may perform processing within the impedance analyzer, e.g. allowing to derive impedance values. The processor also may be adapted for determining the amount and/or allocation of point mutation(s) within the target DNA and/or RNA by calculating the denaturation-time constant based on the difference between the first and second impedance value and corrected for the impact of the chemical by the value representative for such impact.

Such calculating may be performed based on predetermined algorithms, using look up tables, or based on a neural network. Such processor may be a software based processor, as well as a hardware based processor. Calculation of the denaturation-time constant may be based on the theoretical considerations as set forward above. Further features and advantages similar as described for the methods of the first aspect may be obtained by the components described above or by optional additional components providing the functionality of steps of the methods as described in the first aspect.

In a third aspect, the present invention relates to a controller for controlling a bio-sensing device suitable for the detection of DNA and/or RNA and/or the characterization (allocation) of point mutations in DNA and/or RNA. The controller according to embodiments of the present invention is being programmed for providing control signals to the bio-sensing device for contacting a functionalized surface which is coated with probe DNA and/or RNA whereto target DNA and/or RNA duplexes are attached with an electrolytic solution having a neutral pH in a flow cell and measuring a first impedance value within said electrolytic solution. The controller furthermore is being programmed for providing control signals for adding a chemical to the electrolytic solution which is able to achieve denaturation of the target DNA and/or RNA, and then measuring a second impedance value within the flow cell after completion of the denaturation of the DNA and/or RNA target. The controller furthermore is adapted for providing control signals for obtaining a value representative for the impact of the chemical on the impedance of the electrolytic solution, and then and determining the amount and/or allocation of point mutation(s) within the target DNA and/or RNA by calculating the denaturation-time constant based on the difference between the first and second impedance value and corrected for the impact of the chemical by the value representative for such impact. Such a controller may be implemented in software as well as in hardware. It therefore may be a computer program product, e.g. run on a processor. Such a controller also may be a component of the biosensing device as described above.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

EXAMPLES

The following examples illustrate the preparation and functionalization of the sensor substrate suitable to perform the impedimetric measurements of the present invention.

Furthermore examples are added to compare the conversion of the deconvolution of the impedimetric signals using the impedrimetric method of the present invention into the time constant for NaOH exposure and the intrinsic denaturation-time constants with results obtained from optical denaturation. The fitting and very good correspondence with the denaturation results obtained with state of the art optical denaturation methods gives clear evidence that the denaturation times obtained with the impedrimetric method according to the present invention is a reliable alternative technique.

Example 1

Preparation of the Sensor Substrate (Electrodes) and Functionalization of Said Substrate with Probe DNA Diamond-based sensor substrates (electrodes) such as nanocrystalline diamond (NCD) were selected because this material was known to be intrinsically biocompatible and to allow for the covalent immobilization of biochemical receptors by various techniques. Examples are the binding of proteins and DNA fragments [Yang et al., Angewandte Chemie—International Edition 47, p 5183 (2008)], where a manifold of denaturation-rehybridization cycles has been demonstrated without loss of binding capacity. An overview of functionalization strategies, both on oxygen- and on hydrogen terminated diamond surfaces, can be found in the review article by Wenmackers et al. [Wenmackers et al., Physica Status Solidi (a) 206, p 391 (2009)]. Furthermore, diamond offers a wide electro-chemical window and it is chemically and physically stable at elevated temperatures, under extreme pH conditions, and in solutions with high ionic strengths. These elements make NCD a universal electrode material for monitoring biochemical reactions in real time. DNA-hybridization sensors based on diamond as a platform material have been reported in combination with impedance spectroscopy [Gu et al., Journal of Physical Chemistry B 109, p 13611 (2005)], solution-gate FETs [Kuga et al., IEEE International Electron Devices Meeting 2008, Technical Digest, p 483 (2008)], and cyclic voltammetry with a redox mediator on diamond nanowires [Yang et al., Angewandte Chemie—International Edition 47, p 5183 (2008)]. Here, the planar sensor electrodes were prepared by plasma-enhanced chemical vapour deposition (PE-CVD) from methane/hydrogen mixtures in an ASTEX-type reactor as described by Williams et al. [Williams et al., Diamond and Related Materials 17, p 1080 (2008)]. The substrates were 2-inch silicon wafers (thickness 500-550 µm, crystalline orientation (100), p-type doped with resistivities from 1 to 20 $\Omega$cm), which were diced into samples of 10 mm by 10 mm after deposition. The diamond layers had a typical thickness of 100 nm with an average grain size of 50 nm as determined by x-ray diffraction. Due to the nanocrystalline character of the diamond coating, no preferential crystallographic orientation was detectable. To ensure a good electrical conductivity of the diamond layer (range of 1 $\Omega$cm), the PE-CVD deposition was done with an admixture of trimethyl borane (B(CH3)3) to the CH4 gas with a concentration ratio of 200 ppm B/C. The as-prepared diamond electrodes were hydrogenated in H2 plasma (50 Torr, 800° C., power 4000 W, duration of 14 min) to facilitate the attachment of the fatty-acid linker molecules as described in the next paragraph. In total, 5 different diamond electrodes have been studied, denoted as # DI to # D5.

Example 2

Tethering of the Probe DNA to the Functionalized Sensor Substrate and Hybridization of Target DNA to the Probe DNA First, 10-undecenoic fatty acid was photochemically attached to the H-terminated NCD electrodes by UV illumination (wavelength 254 nm, intensity 265 mW/cm2) during 20 hours under a protective $N_2$ atmosphere. The reaction mechanism is presumably based on the fact that the hydrophobic C=C end of the fatty acid is oriented towards the H-terminated diamond surface and mediated by photoemission from the surface as proposed for the photochemical grafting of alkenes to silicon surfaces [Wang et al., Journal of the American Chemical Society 132, p 4048 (2010)]. After this photochemical treatment, the samples were thoroughly rinsed in acidic acid at 100° C. to remove unbound fatty-acid fragments. In a second step, NH2-modified ssDNA (36-mer with the sequence 5'-$NH_2$—C6H12 AAA AAA ACC CCT GCA GCC CAT GTA TAC CCC CGA ACC-3' (SEQ ID NO: 1)) was covalently linked to the COOH group of the fatty acid using carbodiimide coupling. The details of this procedure and the final washing steps to remove non-reacted probe DNA have been published in the references [Vermeeren et al., Langmuir 24, p 9125 (2008)]. The origin and composition of chemical agents and buffer solutions is given in the supporting material, paragraph 8.1. Concerning the probe DNA, the first 7 adenine bases at the 5' terminus serve as a spacer to avoid border effects at the proximity of the electrode surface. The total amount of probe ssDNA used to functionalize 1 $cm^2$ of electrode surface was 300 pmol. This is in excess of the binding capacity of the surface, but it ensures a rapid functionalization due to the high concentration of available probe DNA.

Hybridization of the probe ssDNA molecules (36 bp) attached to the NCD was performed by incubating ssDNA-modified NCD samples for 2 hours at 30° C. with 600 pmol of Alexa 488-labelled target ssDNA (29 bp) in IOx polymerase chain reaction (PCR) buffer. Four different types of target DNA have been employed: a sequence, which was complementary to the probe ssDNA, a random sequence, and two sequences with a 1-base mismatch at base pair 7 or base pair 20 respectively. For a full overview of the different sequences see Table 1. Note that for both 1-base mismatch sequences the mismatch is a 'CC' while the nearest neighbours are 'GC' and 'AT' in both cases. During hybridization, the samples were placed in a closed container under a saturated water vapour atmosphere to avoid evaporation of the reaction fluid. After hybridization, the samples were rinsed in $2^x$ Saline Sodium Citrate (SSC) buffer containing 0.5% SDS for 30 min at room temperature, followed by two 5 min rinsing steps in 0.2×SSC buffer, once at 5 degrees below the hybridization temperature and once at room temperature. From previous studies based on fluorescence intensity and spectroscopic UV ellipsometry, it is known that the areal density of immobilized DNA duplexes is 1012/cm2 and the typical tilt angle with respect to the electrode surface is ~50° [Vermeeren2008]. The areal density corresponds to an average distance of 10 nm between neighbouring DNA strands, which is slightly less than the length of the probe-DNA fragments (36 bases correspond to 12 nm), but still corresponding to a diluted molecular brush without sterical hindering.

TABLE 1

Compilation of the base sequences of the probe DNA and the four different types of target DNA employed in the hybridization and denaturation experiments.

| NameName | Sequence |
|---|---|
| Probe DNA | 3'-CCA AGC CCC CAT ATG TAC CCG ACG TCC CCA AAA AAA $C_6H_{12}$—$NH_2$-5' (SEQ ID NO: 1) |
| Full match | 5'-Alexa 488-$C_6H_{12}$ GGT TCG GGG GTA TAC ATG GGC TGC AGG GG-3' (SEQ ID NO: 2) |
| Mismatch at BP 7 | 5'-Alexa 488-$C_6H_{12}$ GGT TCG GGG GTA TAC ATG GGC TCC AGG GG-3' (SEQ ID NO: 3) |
| Mismatch at BP 20 | 5'-Alexa 488-$C_6H_{12}$ GGT TCG GGG CTA TAC ATG GGC TGC AGG GG-3' (SEQ ID NO: 4) |
| Random sequence | 5'-Alexa 488-$C_6H_{12}$ TCA AAT TGC CAG AAC AAC TAC TGA CTG AA-3' (SEQ ID NO: 5) |

Example 3

Comparative Impedimetric and Optical Denaturation Study

Figure 2:
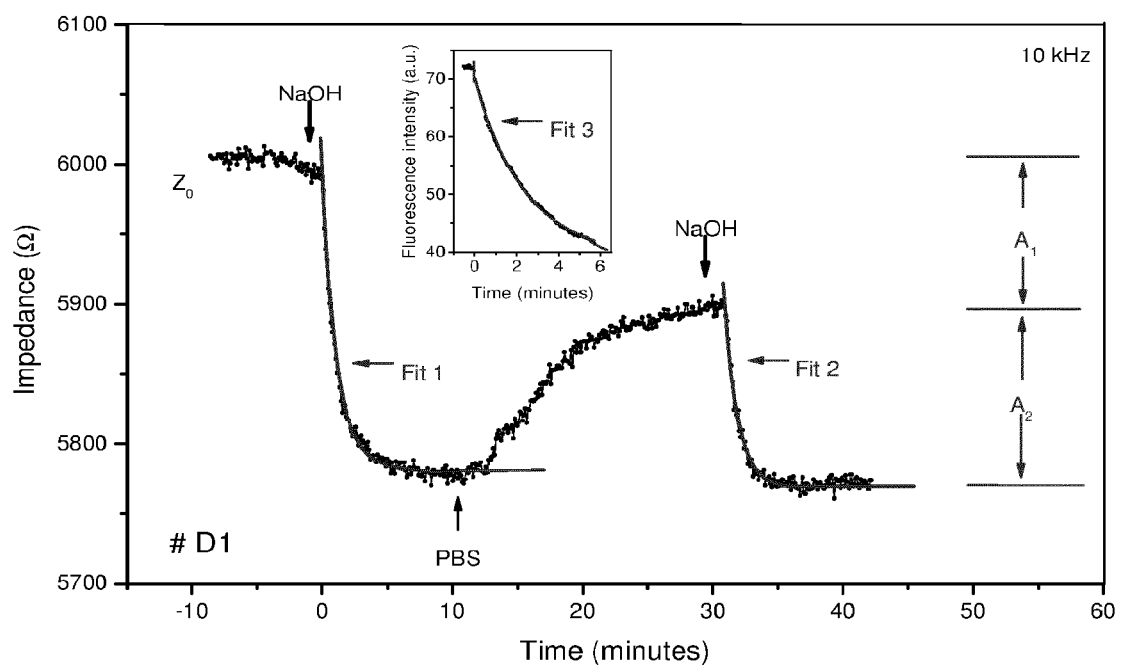
FIG. 2 illustrates the deconvolution of the impedimetric denaturation signal (Fit equation 1) into the intrinsic, DNA-related contribution and the effect of substituting PBS buffer by NaOH (see Fit equation 2) according to an exemplary embodiment of the present invention. Fit equation 3 refers to the fluorimetric control experiment. To crosscheck the electronically determined $\tau 1$, dynamic fluorescence imaging is performed during the denaturation step. Fit equation 3 provides the actual denaturation time which is used to compare $\tau 1$ to $\tau 3$. At t0 0.01 M NaOH enters the cell and replaces the 1×PBS buffer. This leads to a drop of the fluorescence intensity and the impedance. The impedance response emerges from the denaturation and the change of liquids, while the fluorescence drop stems from DNA denaturation only. The extraction of the time constants $\tau 1$ (denaturation) and $\tau 2$ (exchange of fluids) is based on Fit equations 1 and 2. The impedimetric data is consistent with the fluorimetric data obtained from Fit equation 3.
Figure 3A:
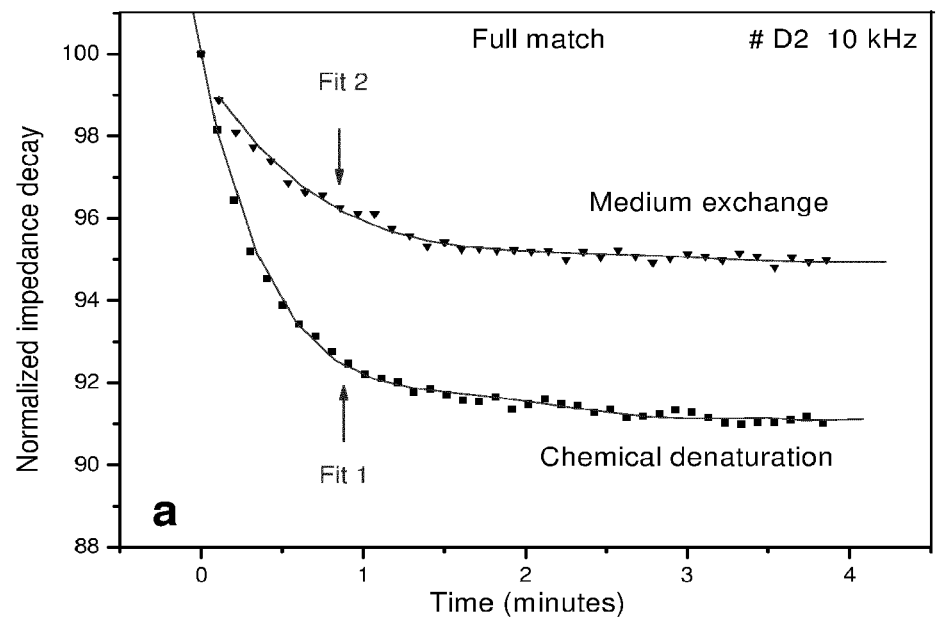
FIG. 3A to FIG. 3D illustrates the impedance decay according to embodiments of the invention performed on a diamond sample (# D2) coated with complementary target DNA (FIG. 3A), coated with complementary target DNA having a mismatch at base pair 20 (FIG. 3B), coated with complementary target DNA having a mismatch at mismatch at base pair 7 (FIG. 3C), and coated with target DNA a random target sequence (FIG. 3D). All data described as 'chemical denaturation' are normalized to the impedance value at the moment when 0.1 M NaOH enters the cell and fitted with the double exponential Equation 1 [1] as described in the text. The curves denoted as 'medium exchange' refer to the second replacement of PBS by 0.1 M NaOH after the actual denaturation step. These data are normalized with respect to the equilibrium impedance value obtained after refilling the cell with PBS buffer (according to Fit equation [2])
Figure 3B:
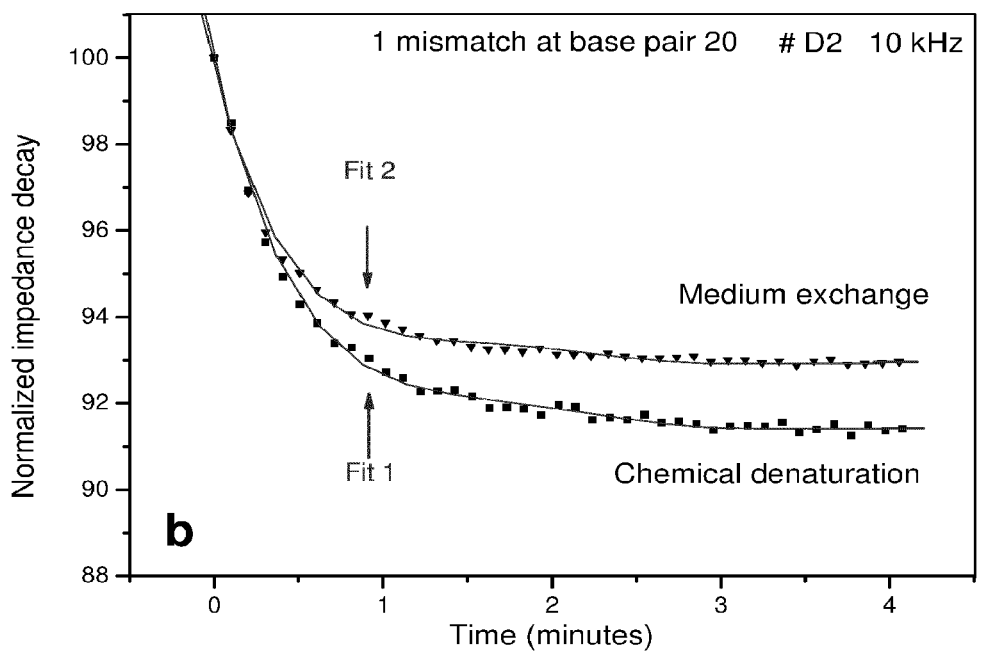
Figure 3C:
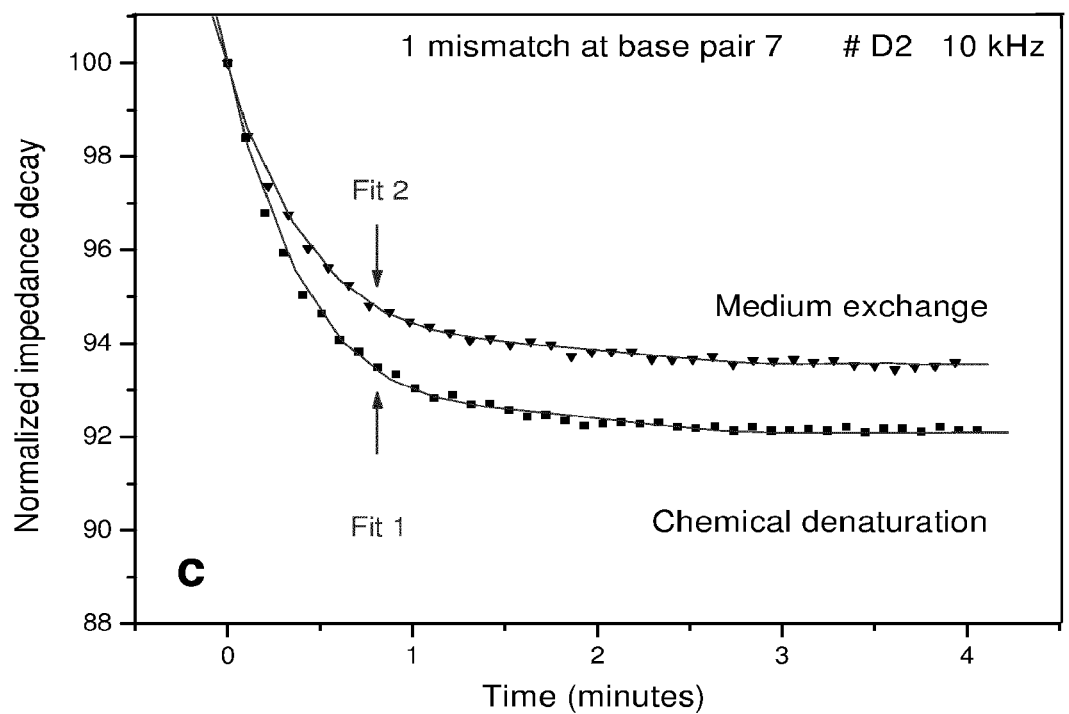
Figure 3D:
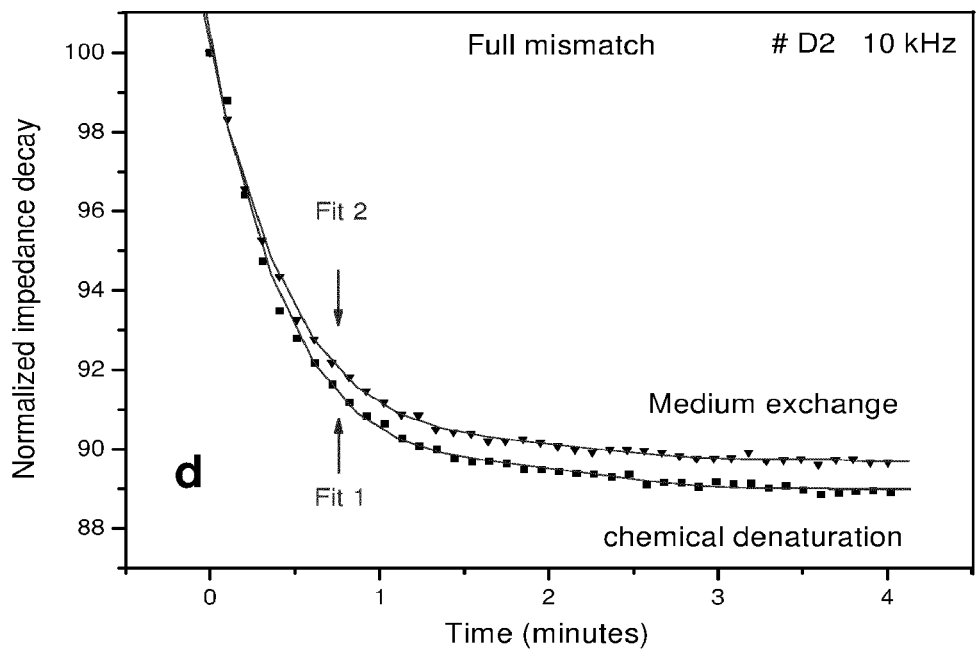

A real-time denaturation experiment on perfectly matched ds DNA (electrode # D1) is exemplarily shown in FIG. 2. After mounting of the functionalized electrode, the cell was filled with PBS buffer and installed on the confocal fluorescence microscope. The cell was allowed to stabilize for 45 min to guarantee that drift effects were absent and the noise level was below 0.5%. The moderate noise level in this measurement is related to the fact that the ambient temperature of about 25° C. could not be actively controlled. In all further measurements, not performed under the confocal microscope, the ambient temperature and temperature of all liquids were strictly stabilized to 19.3° C., resulting in even lower noise levels. At t0=0 min, 0.1 M NaOH at a flow rate of 250 µl per minute enters the cell and replaces the PBS filling. This results in an impedance drop, which consists of two separate contributions: i) the intrinsic effect of denaturation, which affects the electronic properties in the vicinity of the topmost diamond layer and ii) the medium exchange as the 0.1 M NaOH filling causes a higher conductivity than PBS. To distinguish both contributions quantitatively, the 0.1 M NaOH was replaced by reintroducing PBS at tI=12 min (flow rate 250 µl/min.). The impedance increases and stabilizes at a plateau with a lower value as compared to the starting condition. This demonstrates that the impedimetric properties of the electrode surface must have changed upon denaturation because the ionic properties of the PBS buffer are identical before and after the in between denaturation step. To analyze the typical time scale of introducing 0.1 M NaOH, at t2=30 min the PBS was finally replaced by 0.1 M NaOH at a flow rate of 250 µl/min. The superimposed processes of denaturation and medium exchange can mathematically be described as follows:

$$\text{Fit equation 1: } Z(t) = Z(t = \infty) + A_1 \cdot \exp\left\{-\frac{t}{\tau_1}\right\} + A_2 \cdot \exp\left\{-\frac{t}{\tau_2}\right\} \quad [1]$$

$$\text{Fit equation 2: } Z(t) = Z(t = \infty) + A_2 \cdot \exp\left\{-\frac{t - t_2}{\tau_2}\right\} \quad [2]$$

The double-exponential Fit equation [1] for superimposed, independent decay processes is known e.g. from the decomposition of biomass (tomato leaves) and the mass loss of tomato DNA as a function of time [Pote et al., Chemosphere 61, p 677 (2005)]. The parameter $A_1$ represents the denaturation-related decay amplitude and τ1 the associated time constant; the amplitude $A_2$ refers to the impedance drop by the medium exchange and $\tau_2$ is the corresponding time constant. The Fit equation [2] describes solely the influence of the medium exchange from PBS to 0.1 M NaOH after the denaturation has taken place and is therefore representative for the medium exchange as such. Note that there is no intrinsic reason for the exponential time dependence related to the medium exchange, but the agreement with experimental data is excellent with a $R_2$ value of 0.97 for Fit 2. The exponential time dependence of the splitting of DNA duplexes is naturally inherent to decay processes of non-interacting ensembles. First, we applied Fit 2 and extracted $\tau_2=0.97\pm0.06$ min together with $A_2=112\pm9\Omega$ for the medium exchange effect. Inserting these values into Fit 1 resulted in a denaturation-time constant ii=2.24±0.14 min and an amplitude $A_1=115\pm13\Omega$. The R2 of Fit 1 is 0.94, giving support to the concept of superimposed decay processes.

To cross-check the electronically determined $\tau_1$, dynamic fluorescence imaging was performed during the denaturation step (time interval of 1.4 seconds between subsequent images) and the intensity I(t) was averaged over an area of 900 by 900 μm². Selected images with intervals of 36 seconds, taken during the first 6 minutes of the dynamic imaging, are shown in FIG. 3. We note that there is remnant background intensity 10, which is not vanishing even long after this period, and therefore attributed to reflected laser light. The area-averaged intensity values are shown as an insert in FIG. 2 and described with Fit equation [3]:

$$\text{Fit equation 3: } I(t) = I_0 - I_{DNA} \cdot \exp\left\{-\frac{t}{\tau_3}\right\} \quad [3]$$

The fluorescense-decay time constant $\tau_3=2.41\pm0.05$ min is, within the error margins, perfectly consistent with the electronically determined $\tau_1$. The determination of $\tau_3$ is insensitive to the medium composition and truly reflects the progressing denaturation at the NCD-electrode surface. The Alexa 488 labeled target-DNA fragments, which are removed by NaOH exposure, do not contribute to the fluorescence intensity as they are transported away by the constant NaOH flow and the confocal volume, which is restricted to a distance of less than 4.5 μm from the surface of the NCD electrode. In conclusion, the electronically determined denaturation-time constant $\tau_1$ is a reliable measure for the duration of the chemically induced denaturation process. It is important for the applicability of the approach that the time constant of the medium exchange is shorter than the duration of the denaturation process. In the opposite case (denaturation faster than medium exchange), the medium exchange would be the determining factor for the progressing DNA denaturation, making it more difficult to determine the time constant of the denaturation process. This is a useful aspect in the sense that the medium-exchange time constant can be adjusted in wide ranges by adapting the flow rate of the pumping system to meet conditions in which the medium exchange is considerable faster than the dynamics of biological recognition- or unbinding events.

Repeating the entire procedure on diamond sample # $D_1$, re-hybridized with complementary target-DNA fragments, but measured in a temperature-stabilized environment of 19.3° C. and without laser illumination, gave $\tau_1=2.28\pm0.16$ min and $\tau_2=0.58\pm0.04$ min. The denaturation-time constant is clearly consistent with the measurement at 25° C. while the influence of the medium exchange levels off faster [Cell configuration]. As a next step, the probe DNA was hybridized with target DNA with a single-nucleotide mismatch at base pair 7. This resulted in $\tau_1=1.21\pm0.10$ min and $\tau_2=0.48\pm0.02$ min. As expected, the time constant for the medium exchange is close to identical under identical environmental conditions, but the DNA duplexes with the SNP mutation denature considerably faster than the complementary duplexes. This strongly suggests that the monitoring of chemically-induced denaturation can give an indication for the presence of single-nucleotide polymorphisms.

Example 4

Impedimetric Denaturation Monitoring with Various Types of Target DNA

In order to evaluate the reproducibility of the method and whether it in principal allows to localize and to identify SNPs, we performed systematic studies on four additional diamond electrodes (# D2, # D3, # D4, and #D5). Each DNA-modified electrode was hybridized with four different types of target DNA: the perfect complement, the CC mismatch at base pair 7, the CC mismatch at base pair 20 (further away from the diamond electrode and closer to the distal end of the molecular brush), and a random-type target DNA. The random target can also form transient Watson-Crick pairs but this is limited to a few nucleotides as shown in Table 1. Table 1 illustrates compilation of the base sequences of the probe DNA and the four different types of target DNA employed in the hybridization and denaturation experiments. The probe DNA exhibits a spacer consisting of 7 A-bases while the target DNA fragments carry a fluorescent Alexa 488 label at the 5' end. The position of the mismatches with respect to the probe DNA is underlined and indicated by bold letters.

Figure 4:
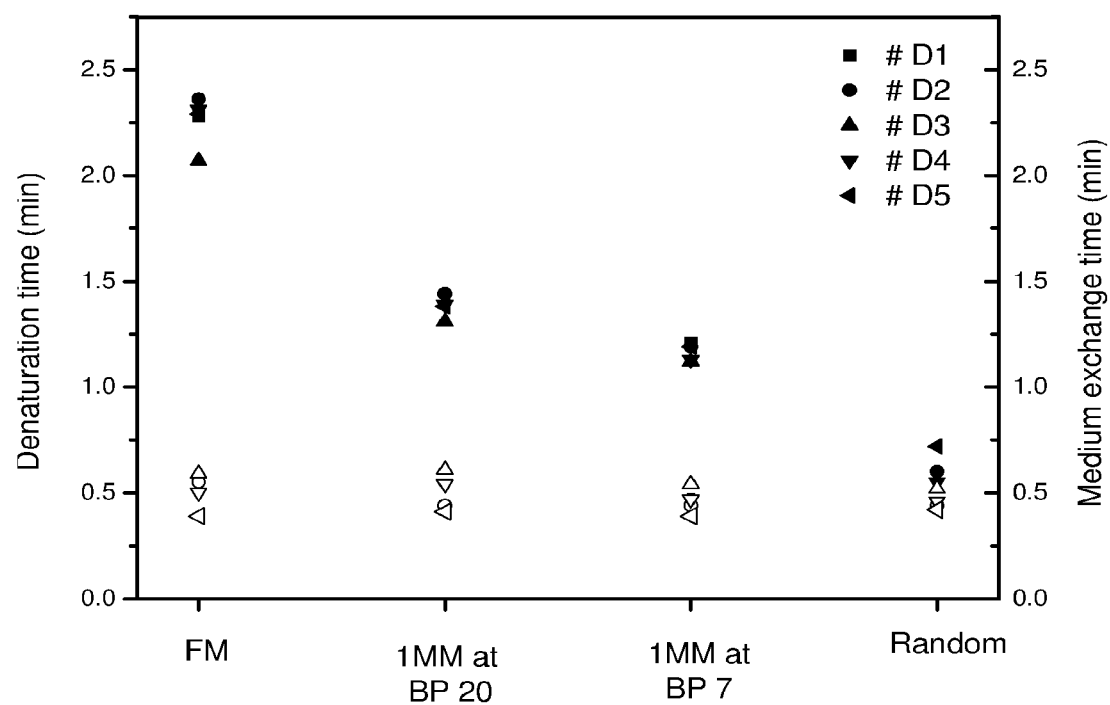
FIG. 4 illustrates the compilation of the denaturation-time constants $\tau 1$ (solid symbols) for the four different types of target DNA according to embodiments of the invention. Each time constant was measured on at least four different diamond electrodes and the scattering between the data is remarkably low. The time constants xI for medium exchange from PBS to 0.1 M NaOH are indicated by open symbols.

Note that during the consecutive hybridizations with the different variants of target DNA, always the initial probe DNA has been used without any regeneration treatment. Exemplarily, the results obtained with electrode # D2 are shown in FIG. 4. All measurements on # D2 (and on # D3, # D4, and # D5) were performed under temperature-stabilized conditions, which resulted in excellent $R_2$ values between 0.96 and 0.996 for the Fit equations [1] and [2]. In FIG. 4, the first impedance decay (additive effect of DNA denaturation and medium exchange) is normalized to the impedance at t=0; the second impedance decay is normalized to the impedance value at the time t2, when the bound DNA has already been denatured and PBS is again replaced by 0.1 M NaOH. All data on the denaturation-time constant $\tau_1$, obtained at 19.3° C. with the five different electrodes, are shown in FIG. 5. The time constants $\tau_2$ for the medium exchange are depicted for comparison. The averaged time-constants for denaturation and medium exchange and the averaged normalized amplitudes are summarized in Table 2 together with their respective standard deviation σ. Table 2 gives a comparison of the theoretical melting temperatures with the parameters deduced from the real-time denaturation experiments. The melting temperatures were calculated using the Fract™ algorithm (values for filter hybridization in brackets) [Fract™, Leber et al., Bioinformatics 21, p 2375

(2005)] and the HYTHER™ algorithm [HYTHER™ version 1.0, available online at http://ozone3.chem.wayne.edu]. The denaturation-time constant $<\tau_1>$, the time constant of the medium exchange $<\tau_2>$, the normalized amplitude $<A_1/Z(0)>$ related to DNA denaturation, and the relative amplitude $<A_2/Z(t2)>$ related to the medium exchange are averages of four to five independent measurements. The σ values are the respective standard deviations. Note that the $<\tau_2>$ values are almost indistinguishable and that $<A_1/Z(0)>$ can be considered as a measure of the quantity of bound target DNA. Concerning $<\tau_1>$, we obtain 2.26±0.11 min for complementary duplexes, 1.38±0.05 min for the mismatch at base pair 20, 1.16±0.04 min for the mismatch at base pare 7, and finally 0.59±0.08 min for the random target. The time constant for denaturation of the random sequence is close to $<\tau_2>$=0.46±0.04 min for the medium exchange, indicating that these fragments are at the most very loosely bound.

TABLE 2

Comparison of the theoretical melting temperatures with the parameters deduced from the real-time denaturation experiments.

| Target DNA: | Complement | Mismatch BP 20 | Mismatch BP 7 | Random |
|---|---|---|---|---|
| T melting (° C.) (Fract ™) | 91 (84) | 85 (78) | 88 (81) | −33 (−41) |
| T melting (° C.) (HyTher) | 79.5 | 75.0 | 76.7 | −50.8 |
| $<\tau_1>$ (min) | 2.26 | 1.38 | 1.16 | 0.59 |
| σ $<\tau_1>$ (min) | 0.11 | 0.05 | 0.04 | 0.08 |
| $<\tau_2>$ (min) | 0.52 | 0.50 | 0.46 | 0.46 |
| σ $<\tau_2>$ (min) | 0.08 | 0.09 | 0.06 | 0.04 |
| $<A_1/Z(0)>$ (%) | 3.4 | 2.0 | 2.0 | 0.4 |
| σ $<A_1/Z(0)>$ (%) | 1.1 | 0.3 | 0.7 | 0.2 |
| $<A_2/Z(t_2)>$ (%) | 4.9 | 6.9 | 5.6 | 9.8 |
| σ $<A_2/Z(t_2)>$ (%) | 1.3 | 0.5 | 1.2 | 1.1 |

To ensure that the marked difference in time constants is not emerging from an electrode-ageing effect during consecutive denaturation processes and exposure to 0.1 M NaOH, the order of hybridization and denaturation with the different types of target DNA was also considered. The samples # D2, # D3, and # D4 were first hybridized with the complementary sequence, second with the mismatch at base pair 7, third with the mismatch at base pair 20, and finally with the random sequence. In case of sample # D5 the order was reversed, starting with the random sequence. As a result, all time constants determined with # D5 were found to be fully in line with the other electrodes.

Since the melting temperature Tm is the established measure for the stability of DNA duplexes and the key parameter in localization and identification of single-nucleotide polymorphisms, we employed two different algorithms to estimate Tm for the four different target-probe duplexes in our study. Fract™ is available online and the underlying principles are known. HYTHER™ is also available online and allows taking into account that the 5' end of the probe DNA is tethered to a solid support. Both algorithms calculate Tm on basis of the sequence of probe- and target DNA, nearest neighbour effects, the concentration of the probe DNA, and the Na$^+$ concentration of the surrounding electrolyte. The numerical results of both algorithms are summarized in Table 2. Despite of minor differences in the absolute Tm values, the global trend is in agreement with the obtained denaturation-time constants: the complementary duplexes have the highest melting temperature and the longest denaturation time, the duplexes with the random sequence have the lowest Tm and shortest τι. Negative $T_m$ values in the case of the random sequence mean that these duplexes are unstable at any positive temperature because the calculations do not take into account the freezing of the aqueous matrix. The melting temperature of the SNP duplexes is reduced by 3 to 6° C. as compared to their fully complementary counterparts while we observe here a strongly decreased denaturation time. Interestingly enough, both algorithms predict a slightly higher stability for the duplex with the SNP at base pair 7 (Tm=76.7° C., calculated with HYTHER) compared to the SNP at base pair 20 (HYTHER: Tm=75.0° C.). This difference is minimal, note that the type of the defect and its nearest neighbours are identical, but our data suggest reproducibly that the duplexes with the SNP at base pair 7 denature slightly faster than those with the SNP at base pair 20. The average denaturation time for the SNP at base pair 20 is 1.38±0.05 min, while this is reduced to 1.16±0.04 min for the SNP position at base pair 7. Within our statistics of four to five independent measurements per defect position, there is no overlapping of error bars and the method seems to allow distinguishing between both positions. This may be explained by the fact that the impedimetric signal is influenced by changes of the ion distribution close to the electrode surface at the scale of the Debye length, being in the order of 1 nm for 0.1 M NaOH. Assuming that chemically-induced denaturation starts preferentially at both ends of a DNA duplex and at the position of mismatches, a mismatch in proximity to the electrode surface may indeed cause a faster response than a more distant defect.

Finally, also the normalized amplitude parameter $<A_1/Z(0)>$ gives information on the amount of bound target DNA. There is a systematic decrease from 3.4% (complementary target), to 2.0% (mismatch at base pair 20 or at base pair 7) and finally to 0.3% for the random sequence, which is close to a zero effect within the standard deviation. Keeping in mind that the hybridization was performed under standardized conditions it is evident that defected sequences bind to a lesser extent than the complementary fragments, which result in duplexes with the highest thermodynamic stability. Except for the random sequence, the normalized $<A_2/Z(t_2)>$ is identical for all samples and sequences within the error margins.

The invention claimed is:

1. A bio-sensing device suitable for the detection of target DNA and/or RNA and/or the characterization (allocation) of point mutations in target DNA and/or RNA, said bio-sensing device comprising at least:
   a flow cell equipped with an impedimetric analyzer,
   a biocompatible and inert substrate disposed against the flow cell, such that at least one surface of said substrate is exposed to liquid flow within the flow cell, said substrate having covalently bound probe DNA and/or RNA on its at least one exposed surface, said probe DNA and/or RNA being configured to bind the target DNA and/or RNA,
   a pumping system and switching valve connected to said flow cell,
   a first liquid supply comprising a electrolytic solution connected to said pumping system and to said switching valve,
   a second liquid supply comprising a chemical that is able to achieve denaturation of DNA and/or RNA such that any of the target DNA and/or RNA that is bound to the probe DNA and/or RNA is released from the probe DNA and/or RNA when exposed to the chemical, the second liquid supply being connected to said pumping system and to said switching valve,
   a means for obtaining a value representative for the impact of the chemical on the impedance of the electrolytic solution said means for obtaining the value representative for the impact of the chemical on the impedance of the electrolytic solution being operatively connected to the impedimetric analyzer, and
   a means for determining the amount of the target DNA and/or RNA and/or an allocation of point mutation(s) within the target DNA and/or RNA by calculating the denaturation-time constant based on the difference between the first and second impedance value and corrected for the impact of the chemical by the value representative for such impact, said means for determining the amount and/or allocation being operatively connected to the means for obtaining the value representative for the impact of the chemical on the impedance of the electrolytic solution.

2. A bio-sensing device according to claim 1, wherein said means for obtaining a value representative for the impact of the chemical on the impedance of the electrolytic solution is a controller programmed for controlling the impedance analyzer and the pumping system and switching valve for removing the chemical from the flow cell by adding electrolytic solution and then measuring a third impedance value within the flow cell to determine the impact of the chemical on the impedance of the electrolytic solution, the third impedance value being the value representative for the impact of the chemical on the impedance of the electrolytic solution.

3. A bio-sensing device according to claim 2, wherein the controller is programmed for providing control signals to the bio-sensing device for:
   contacting the exposed surface on which the probe DNA and/or RNA is bound to which target DNA and/or RNA are duplexed with an electrolytic solution having a neutral pH in a flow cell and measuring a first impedance value within said electrolytic solution, and then
   adding the chemical to the electrolytic solution to achieve denaturation of the target DNA and/or RNA, and then
   measuring a second impedance value within the flow cell after completion of the denaturation of the target DNA and/or RNA, and then
   obtaining a value representative for the impact of the chemical on the impedance of the electrolytic solution, and then
   determining the amount of target DNA and/or RNA and/or allocation of point mutation(s) within the target DNA and/or RNA by calculating the denaturation-time constant based on the difference between the first and second impedance value and corrected for the impact of the chemical by the value representative for such impact.

4. A bio-sensing device according to claim 3, the controller being a computer program product.

5. A bio-sensing device according to claim 1, wherein the flow cell has a volume between 25 μL and 190 μL.

6. A bio-sensing device according to claim 1, wherein the substrate is nanocrystalline diamond, or a semiconductor substrate having a diamond coating 50-150 nm in thickness at its surface exposed to liquid flow within the flow cell.

7. A bio-sensing device according to claim 1, wherein the probe DNA and/or RNA is $NH_2$-modified single stranded DNA (ssDNA).

8. A bio-sensing device according to claim 7, wherein the $NH_2$-modified single stranded DNA is covalently bound to the surface exposed to liquid flow within the flow cell through a fatty acyl group.

9. A bio-sensing device according to claim 1, wherein the chemical that is able to achieve denaturation of DNA and/or RNA is NaOH.

10. A bio-sensing device according to claim 1, herein the flow cell has a volume between 25 μL and 190 μL.

11. A bio-sensing device according to claim 1 wherein the electrolytic solution is a buffer having a neutral pH.

12. A bio-sensing device according to claim 1, wherein the impedimetric analyzer comprises a counterelectrode disposed in the flow cell, and is configured to use the exposed surface on which the probe DNA and/or RNA is bound as the working electrode.

13. A bio-sensing device according to claim 1, wherein
   the impedimetric analyzer comprises a counterelectrode disposed in the flow cell, and is configured to use the exposed surface on which the probe DNA and/or RNA is bound as the working electrode;
   the electrolytic solution is a buffer having a neutral pH; and
   the chemical that is able to achieve denaturation of DNA and/or RNA is NaOH.

14. A bio-sensing device according to claim 13, wherein the probe DNA and/or RNA is $NH_2$-modified single stranded DNA covalently bound to the surface exposed to liquid flow within the flow cell through a fatty acyl group.

15. A bio-sensing device according to claim 14, wherein the substrate is nanocrystalline diamond, or a semiconductor substrate having a diamond coating 50-150 nm in thickness at its surface exposed to liquid flow within the flow cell.

* * * * *

SEQUENCE LISTING

<160> NUMBER OF SEQ ID NOS: 5

<210> SEQ ID NO 1
<211> LENGTH: 36
<212> TYPE: DNA
<213> ORGANISM: Artificial Sequence
<220> FEATURE:
<223> OTHER INFORMATION: Synthetic; Probe DNA
<220> FEATURE:

```
<221> NAME/KEY: modified_base
<222> LOCATION: (1)..(1)
<223> OTHER INFORMATION: 6-aminohexyl modification at 5'

<400> SEQUENCE: 1
aaaaaaaccc ctgcagccca tgtataccccc cgaacc                                    36

<210> SEQ ID NO 2
<211> LENGTH: 29
<212> TYPE: DNA
<213> ORGANISM: Artificial Sequence
<220> FEATURE:
<223> OTHER INFORMATION: Synthetic; full match
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 2
ggttcggggg tatacatggg ctgcagggg                                              29

<210> SEQ ID NO 3
<211> LENGTH: 29
<212> TYPE: DNA
<213> ORGANISM: Artificial Sequence
<220> FEATURE:
<223> OTHER INFORMATION: Synthetic; Mismatch at BP7
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 3 ggttcgggggg tatacatggg ctccagggg                                             29

<210> SEQ ID NO 4
<211> LENGTH: 29
<212> TYPE: DNA
<213> ORGANISM: Artificial Sequence
<220> FEATURE:
<223> OTHER INFORMATION: Synthetic; Mismatch at BP 20
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 4
ggttcggggc tatacatggg ctgcagggg                                              29

<210> SEQ ID NO 5
<211> LENGTH: 29
<212> TYPE: DNA
<213> ORGANISM: Artificial Sequence
<220> FEATURE:
<223> OTHER INFORMATION: Synthetic; random sequence
<220> FEATURE:
<221> NAME/KEY: modified_base
<222> LOCATION: (1)..(1)
<223> OTHER INFORMATION: 6-(Alexa 488 dye)-hexyl modification at 5'

<400> SEQUENCE: 5
tcaaattgcc agaacaacta ctgactgaa                                              29
```